(12) United States Patent  
Thabeth et al.

(10) Patent No.: US 11,994,461 B2
(45) Date of Patent: May 28, 2024

(54) SELF CLEANING OPTICAL PROBE

(71) Applicant: Inov8 Systems Limited, Belfast (GB)

(72) Inventors: Khalid Thabeth, Belfast (GB); Raymond Acheson, Belfast (GB)

(73) Assignee: Inov8 Systems Limited, Belfast (GB)

( * ) Notice: Subject to any disclaimer, the term of this patent is extended or adjusted under 35 U.S.C. 154(b) by 372 days.

(21) Appl. No.: 17/425,369

(22) PCT Filed: Jan. 23, 2020

(86) PCT No.: PCT/EP2020/000024
§ 371 (c)(1),
(2) Date: Jul. 23, 2021

(87) PCT Pub. No.: WO2020/151909
PCT Pub. Date: Jul. 30, 2020

(65) Prior Publication Data
US 2022/0099563 A1 Mar. 31, 2022

(30) Foreign Application Priority Data
Jan. 25, 2019 (GB) ..................... 1901070

(51) Int. Cl.
*G01N 21/15* (2006.01)
*B08B 7/02* (2006.01)
(Continued)

(52) U.S. Cl.
CPC ............ *G01N 21/15* (2013.01); *B08B 7/028* (2013.01); *G01N 21/8507* (2013.01); *G01N 33/1833* (2013.01); *G01N 2021/154* (2013.01)

(58) Field of Classification Search
CPC ........ G01N 21/15; G01N 21/47; G01N 21/53; G01N 21/64; G01N 2021/55;
(Continued)

(56) References Cited

U.S. PATENT DOCUMENTS 5,842,995 A * 12/1998 Mahadevan-Jansen ..................... A61B 5/4331
600/476
7,935,938 B2 4/2011 Thabeth et al.
(Continued)

FOREIGN PATENT DOCUMENTS

CN 204086120 1/2015
JP H01320449 12/1989
(Continued)

OTHER PUBLICATIONS

Commonly assigned co-pending U.S. Appl. No. 18/309,301, filed Apr. 28, 2023, entitled Self-Cleaning Optical Probe.
(Continued)

*Primary Examiner* — Hoa Q Pham
(74) *Attorney, Agent, or Firm* — Gardner, Linn, Burkhart & Ondersma LLP

(57) ABSTRACT

An optical probe includes an optical window for transmitting light therethrough, an ultrasonic transducer for applying ultrasonic vibrations to the optical window for cleaning the optical window, and one or more light guides for transmitting light through the optical window to a measurement region and/or receiving light transmitted through the optical window from the measurement region. The ultrasonic transducer is coupled to the optical window via an elongate body adapted to transmit ultrasonic vibrations from the ultrasonic transducer to the window. The light guides communicate with the optical window adjacent the elongate body. An additional lens or light filter may be mounted adjacent the measurement window and/or the window itself may be adapted to incorporate a lens and/or light filter.

16 Claims, 5 Drawing Sheets

(51) Int. Cl.
*G01N 21/85* (2006.01)
*G01N 33/18* (2006.01)

(58) Field of Classification Search
CPC ......... G01N 33/1833; G01N 2021/154; G01N 21/8507; B08B 3/04; B08B 3/02; B08B 5/00; B08B 7/028; G02B 27/0006; H01J 5/16
USPC .......... 356/445–448, 241.1, 241.2, 241.6, 72
See application file for complete search history.

(56) References Cited

U.S. PATENT DOCUMENTS

| | | |
|---|---|---|
| 2002/0167664 A1 | 11/2002 | Rettig et al. |
| 2008/0030714 A1* | 2/2008 | Hall ................. B08B 17/02 356/73.1 |
| 2009/0253964 A1* | 10/2009 | Miyamoto ......... A61B 1/00091 600/157 |
| 2009/0264701 A1 | 10/2009 | Ito |
| 2011/0259378 A1 | 10/2011 | Skeidsvoll et al. |
| 2011/0313253 A1 | 12/2011 | Ito |
| 2012/0255361 A1* | 10/2012 | Thabeth ................. G01N 21/15 73/655 |
| 2015/0260639 A1* | 9/2015 | Thabeth ................. G01N 21/64 134/184 |
| 2015/0285733 A1* | 10/2015 | Henriksen ............. B08B 7/028 134/1 |
| 2016/0025617 A1 | 1/2016 | Magnussen et al. |
| 2018/0128746 A1 | 5/2018 | Zhang |
| 2020/0086346 A1* | 3/2020 | Kobrin ............... G02B 27/0006 |

FOREIGN PATENT DOCUMENTS

| | | |
|---|---|---|
| JP | H05329156 A | * 12/1993 |
| WO | 2008015390 | 2/2008 |
| WO | 2009134145 | 11/2009 |
| WO | 2011047813 | 4/2011 |

OTHER PUBLICATIONS

International Search Report of corresponding PCT Application No. PCT/EP2020/000024, dated May 13, 2020.

* cited by examiner

SELF CLEANING OPTICAL PROBE

CROSS REFERENCE TO RELATED APPLICATIONS

The present application is a § 371 national stage of International Application PCT/EP2020/000024, filed Jan. 23, 2020, which claims priority benefit to U.K. Pat. Application Ser. No. 1901070.1, filed Jan. 25, 2019, both of which are hereby incorporated herein by reference in their entireties.

FIELD OF THE INVENTION

This invention relates to a self cleaning optical probe and in particular to a self cleaning optical probe for oil in water analysers.

BACKGROUND OF THE INVENTION

There are many applications that require measurement of the quantity of oil and/or the identification of oil or other contaminants present in a liquid. For example, in pipes leading from oil production or refining facilities or the like it may be required to measure the amount of oil and/or the identity of oil present in the liquid (mainly water) flowing in the pipes. Oil in water analysers or probes are used for this purpose, either in side stream passages or as insertion probes.

Oil has a natural fluorescence. Therefore oil in water analysers typically measure the quantity of oil present in water by the detection of fluorescence. Devices that detect and/or measure fluorescence are commonly referred to as fluorometers. A fluorometer usually includes a light source for causing fluorescence in a target substance and a detector for measuring the resultant fluorescence.

A typical in-line or side stream oil in water analyser has a measurement window forming a portion of a wall of a measurement region through which the excitation light source is transmitted into the measurement region and through which the resultant fluorescent and/or reflected light is received to be analysed in order to determine the quantity and/or identify of oil and/or other contaminants present. In insertion probes a measurement window is provided at a distal end of the probe. One problem with both types of devices is the fouling of the measurement window by oil and other substances within the measurement region. This problem may be addressed by using an ultrasonic transducer, whereby the measurement window can be cleaned by ultrasonic cavitation created by the ultrasonic energy transmitted to the measurement window from the ultrasonic transducer.

A known optical probe of an oil in water analyser comprises an elongate hollow probe shaft (known as a sonitrode) having a sapphire window (defining the measurement window) at a distal end thereof. Ceramic transducer discs are mounted on an opposite end of the probe shaft, located between a back mass and the probe shaft. A bolt typically passes through the rear of the back mass and through the ceramic transducer discs into the rear end of the probe shaft to secure the ceramic discs and back mass to the probe shaft.

Optical fibres and electrical leads are typically passed through a central channel of the hollow probe shaft, typically via an entry slot cut through side of the probe shaft or through a hollow bolt securing the back mass to the transducer discs. The central channel through the hollowed probe in itself introduces large inefficiencies in the transmission of ultrasonic energy. Furthermore, where provided, entry slots in the side of the probe shaft create additional impedance to the transmission of ultrasonic energy from the ceramic transducer discs through the probe shaft to the sapphire measurement window. These inefficiencies and impedances in the overall length of the hollow probe shaft impact the efficiency of the sonic energy transmission, resulting in poor energy transmission from the ceramic transducer discs to the sapphire window and in turn the necessity for greater energy to overcome these losses.

SUMMARY OF THE INVENTION

According to one form of the present invention there is provided an optical probe comprising an optical window for transmitting light therethrough, an ultrasonic transducer for applying ultrasonic vibrations to the optical window for cleaning the optical window, and one or more light guides for transmitting light through the optical window to a measurement region and/or for receiving light transmitted through the optical window from the measurement region, wherein the ultrasonic transducer is coupled to said optical window via an elongate body adapted to transmit ultrasonic vibrations from the ultrasonic transducer to the window, wherein the one or more light guides communicate with the optical window adjacent said elongate body. Optionally at least the distal end of the one or more light guides extends alongside the elongate body.

The ultrasonic transducer may be mounted against a first end of the elongate body, a second end of the elongate body, opposite the first end, being mounted against the optical window or against an intermediate member located between the elongate body and window. The second end of the elongate body may engage a substantially central region of the optical window or the intermediate member. The one or more light guides may be mounted in the intermediate member to cooperate with the optical window.

Optionally, at least a portion of the optical window and/or a further optical member adjacent the optical window is adapted to modify light passing through the optical window. The optical window and/or the further optical member may comprise or incorporate at least one lens. The optical window and/or the further optical member may incorporate or may be associated with mirror surfaces configured to modify light passing through the optical window. The optical window and/or the further optical member may incorporates or be associated with a filter adapted to pass specific wavelengths of light while blocking others.

In one embodiment the ultrasonic transducer may comprise one or more ceramic transducer elements and a reaction mass mounted against the one or more ceramic transducer elements. The ultrasonic transducer elements and reaction mass may be secured to the first end of the elongate body by means of a fastener passing therethrough.

At least a distal portion of the one or more light guides may extend substantially parallel to the elongate body.

Optionally, the one or more light guides comprise one or more optical fibres.

Optionally, the elongate body comprises a tubular or cylindrical member having a diameter less than the diameter of the optical window such that the elongate body cooperates with a central region of the optical window to transmit ultrasonic vibrations thereto. The one or more light guides may cooperate with a peripheral region of the optical window outside of the central region of the optical window.

Optionally, the elongate body comprises a solid shaft whereby ultrasonic energy is transmitted therethrough with minimum energy loss.

In one embodiment a distal end of the one or more light guides may be adapted to modify light passing therethrough. The distal end of the one or more light guides may comprise an interference lens.

These and other objects, advantages and features of the invention will become apparent upon review of the following specification in conjunction with the drawings.

BRIEF DESCRIPTION OF THE DRAWINGS

Embodiments of the present invention will now be illustrated, by way of example, with reference to the accompanying drawings, in which:—

DETAILED DESCRIPTION OF THE DRAWINGS

Figure 1:
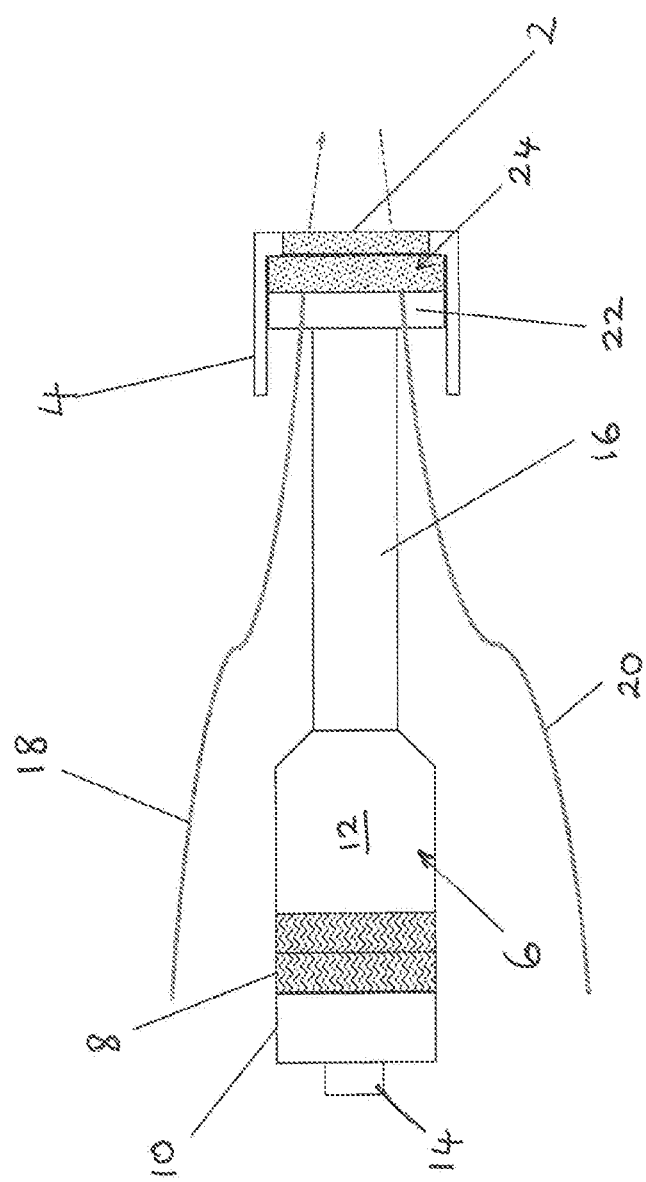
FIG. 1 is a longitudinal sectional view through an optical probe in accordance with a first embodiment of the present invention.

As illustrated in FIG. 1, an optical probe in accordance with a first embodiment of the present invention comprises a measurement window 2, defining a distal end of an insertion probe or alternatively a wall portion of a measurement region of a side stream oil in water analyser, the measurement window being mounted in a window holder 4, which may comprise a portion of a housing of the probe.

An ultrasonic transducer 6 is provided for transmitting ultrasonic energy to the measurement window 2 in order to clean the window. The ultrasonic transducer may comprise one or more ceramic transducer discs 8 located between a back mass 10 and a transducer body 12. A bolt 14 preferably passes through the rear of the back mass 10 and through the ceramic transducer discs 8 into the rear end of the transducer body 12 to secure the ceramic discs 8 and back mass 10 to the transducer body.

The ultrasonic transducer 6 is mechanically coupled to the measurement window 2 via a solid cylindrical probe shaft 16 extending therebetween.

Light guides 18,20, in the form of optical fibres, extend alongside the probe shaft 16, distal ends of light guides 18,20 being mounted in an intermediate plate 22, secured between the probe shaft 16 and measurement window 2 within the window holder 4, whereby the light guides 18,20 are located adjacent and alongside the probe shaft 16 to transmit and received light through the measurement window 2. This avoids the need for a hollow probe shaft 16. The solid cylindrical probe shaft 16 extending between the ultrasonic transducer 6 and the measurement window 2 minimises any loss of energy between the two and therefore greatly reduces the energy consumption of the ultrasonic transducer 6 required for the creation of cavitation and efficient cleaning of the measurement window 2.

Furthermore, the location of the light guides to the side of the probe shaft, and therefore to a side region of the window advantageously increases the useful life of the measurement window. This is because ultrasonic energy from the ultrasonic transducer is highest in a central region of the measurement window (i.e. along the central axis of the probe shaft 16), reducing towards the outer edges of the window. Therefore cavitation is greatest in this central region, leading to erosion and etching of this central region of the window.

In prior art devices, where the light guides pass down a central bore in the probe shaft, the light guides receive and transmit light through this central region of greatest erosion, leading to early replacement of the window once significant erosion and etching of this central viewing region occurs. In an optical probe in accordance with the present invention the light guides interact with the measurement window in a side region, offset from this central region of greatest and most rapid erosion, this side viewing region being exposed to lower levels of ultrasonic energy and minimal erosion. Therefore the useful life of the measurement window is greatly extended.

In the embodiment shown in FIG. 1, a lens 24 is provided between the intermediate plate 22 and the window 2. This lens 24 can be adapted modify the light passing into and out of the light guides 18,20 as required such that the light can be focused or redirected towards specific locations within the measurement region, for example towards a central portion of the measurement region, while ultrasonic energy from the ultrasonic transducer 6 is efficiently transmitted via the solid probe shaft 16 to the measurement window 2 via the intermediate plate 22 and the lens 24.

Figure 2:
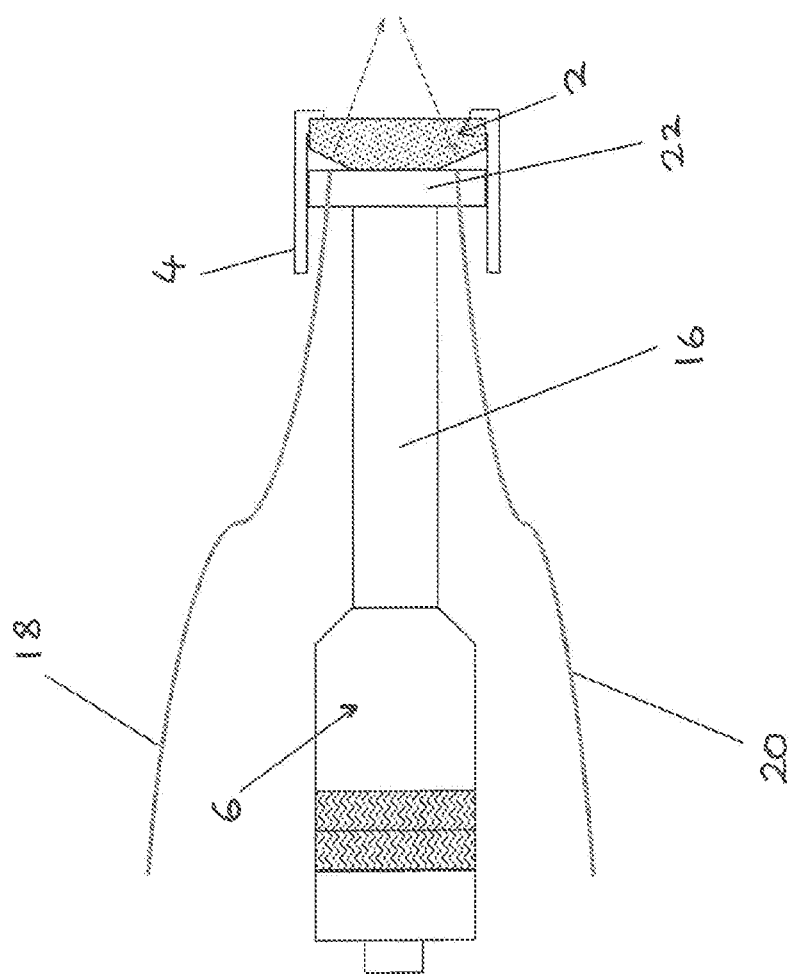
FIG. 2 is a longitudinal sectional view through an optical probe in accordance with a second embodiment of the present invention.

In an alternative embodiment, illustrated in FIG. 2, the measurement window 2 may itself may be adapted to define a lens adapted to modify light passing therethrough, for example to focus light towards a specific location, such as the centre of the measurement region, omitting the need for a further lens. In such embodiment, ultrasonic energy from the ultrasonic transducer 6 is transmitted through the solid probe shaft 16 to the measurement window 2 via the intermediate plate 22 in direct contact with the measurement window 2, both the intermediate plate 22 and measurement window 2 being mounted within the measurement window holder 4. Again, light guides 18,20 are mounted in the intermediate plate 22 to extend alongside the probe shaft 16.

Figure 3:
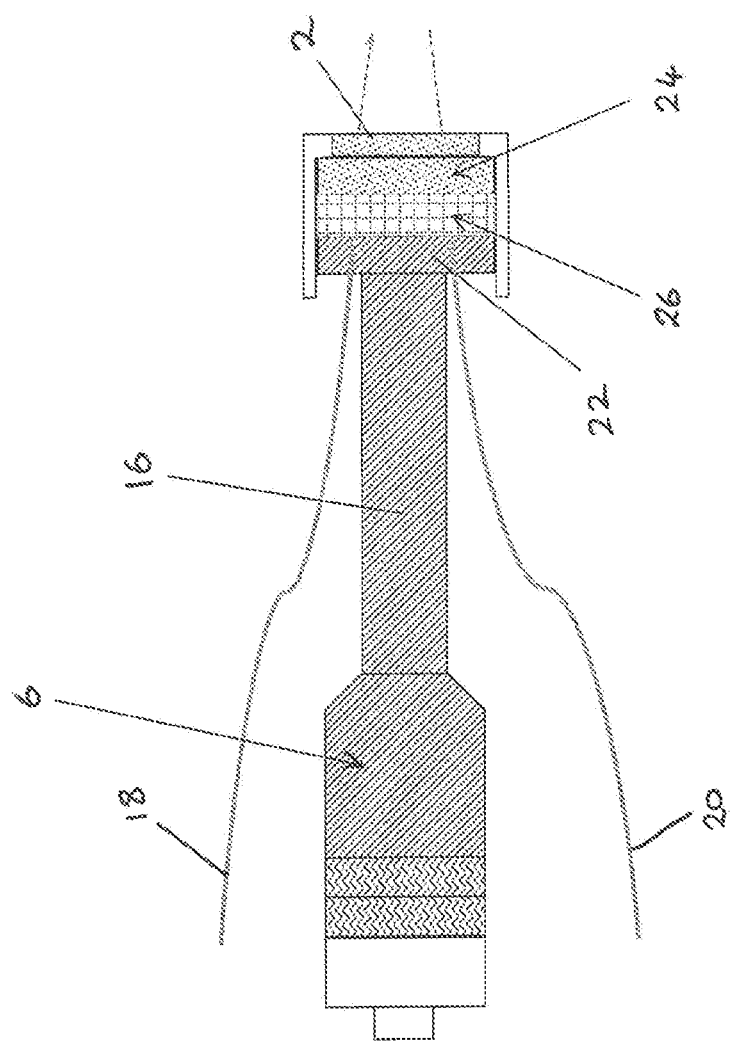
FIG. 3 is a longitudinal sectional view through an optical probe in accordance with a third embodiment of the present invention.

As illustrated in FIG. 3, in an alternative embodiment, in addition to a lens 24, a filter 26 may be located between the intermediate plate 22 and the measurement window 2, said filter being configured to pass light of specific wavelengths while blocking others passing between the measurement window 2 and light guides 18,20. Ultrasonic energy from the ultrasonic transducer 6 is transmitted to the window 2 via the solid probe shaft 16, intermediate plate 22 and both the lens 24 and filter 26. It is envisaged that the measurement window 2 may also be adapted to comprise a filter, adapted to block specific wavelengths of light while transmitting others, as well as or instead of defining a lens.

Figure 4:
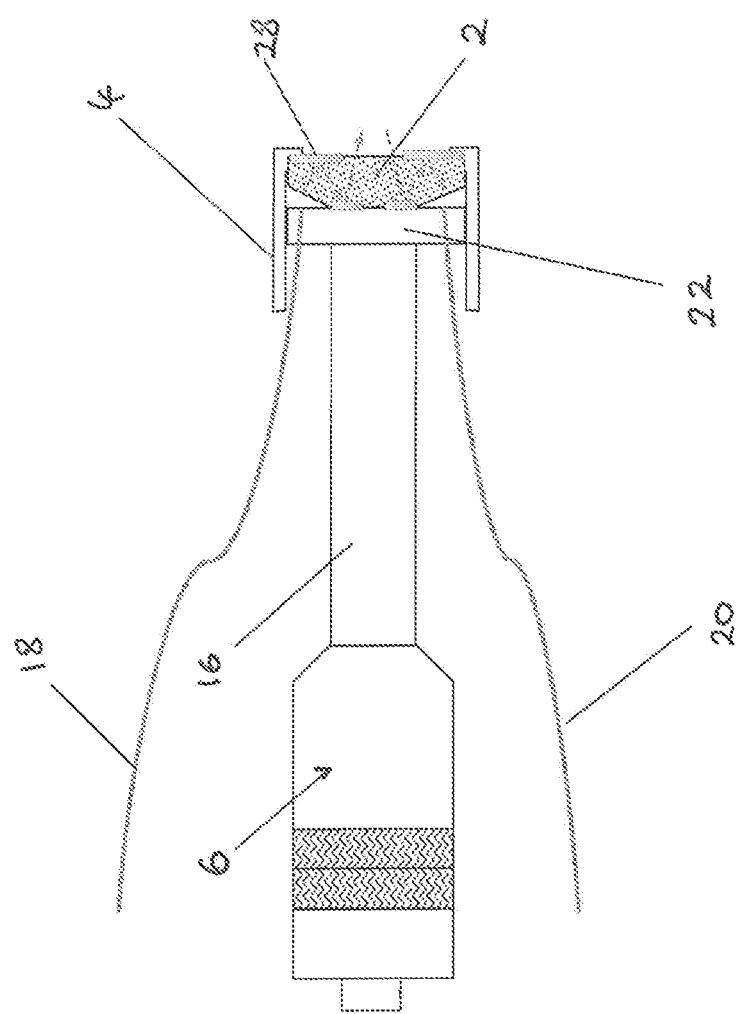
FIG. 4 is a longitudinal sectional view through an optical probe in accordance with a fourth embodiment of the present invention.

As illustrated in FIG. 4, the measurement window 2 may define a mirrored lens, having mirror surfaces 28 configured to focus or otherwise modify or redirect light passing through the window 2.

Figure 5:
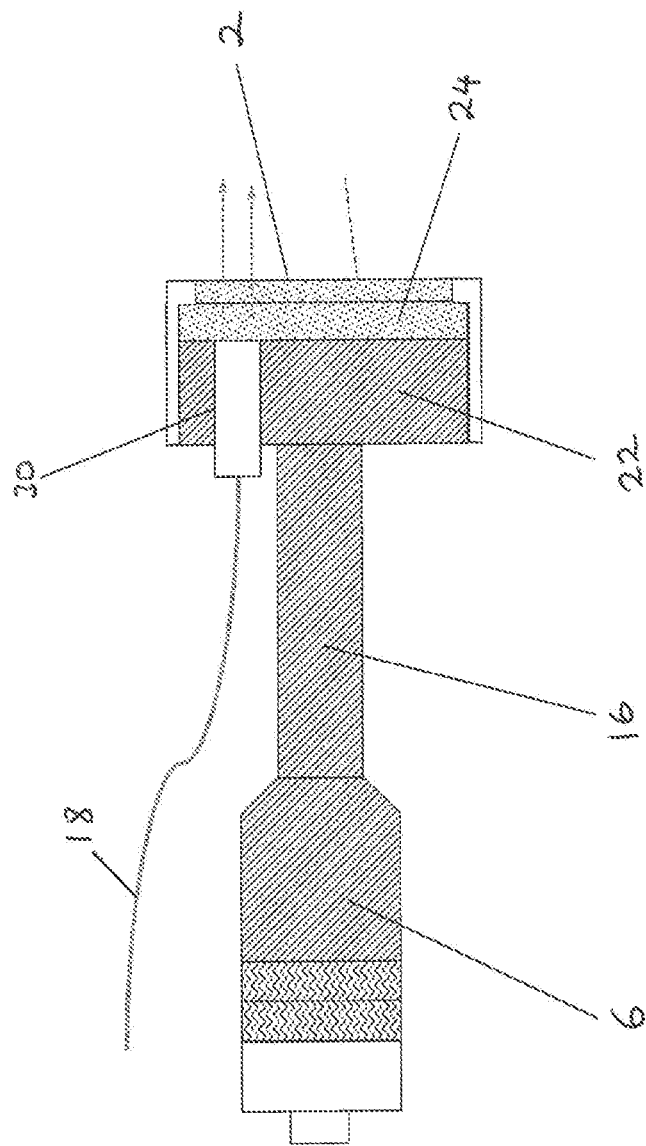
FIG. 5 is a longitudinal sectional view through an optical probe in accordance with a fifth embodiment of the present invention.

In a further embodiment, illustrated in FIG. 5, an additional interference lens or filter may be provided within the intermediate plate 22 at a distal end of one or more of the light guides 18 to provide further modification and/or filtering of the light passing to and from said specific light guides 18, in addition to a lens 24, and/or filter 26 and/or light modification features of the window 2.

Such an optical probe construction in accordance with the present invention facilitates the insertion of numerous devices such as optical sensors, cameras, light sources, etc., effectively creating a generic self cleaning carrier probe that will facilitate the insertion of various devices into fluid environments, negating the need for additional routine cleaning.

The invention is not limited to the embodiments described herein but can be amended or modified without departing from the scope of the present invention, which is intended to be limited only by the scope of the appended claims as interpreted according to the principles of patent law including the doctrine of equivalents.

The invention claimed is:

1. An optical probe comprising:
an optical window for transmitting light therethrough;
an ultrasonic transducer operable to apply ultrasonic vibrations to said optical window for cleaning said optical window;
one or more light guides for transmitting light through said optical window to a measurement region or for receiving light transmitted through said optical window from said measurement region; and
an elongate body comprising a solid shaft having a first end positioned at said ultrasonic transducer and a second end proximate said optical window, wherein when said ultrasonic transducer is energized said solid shaft transmits ultrasonic vibrations along its length from said ultrasonic transducer to said optical window;
wherein said ultrasonic transducer is coupled to said optical window via said elongate body;
wherein at least a distal end of said one or more light guides extends alongside said elongate body; and
wherein said one or more light guides communicate with said optical window adjacent said elongate body.

2. The optical probe of claim 1, wherein:
said ultrasonic transducer is mounted against said first end of said elongate body; and
said second end of said elongate body is mounted against said optical window or against an intermediate member located between said elongate body and said optical window.

3. The optical probe of claim 2, wherein said second end of said elongate body engages a substantially central region of said optical window or said intermediate member.

4. The optical probe of claim 2, wherein said optical probe comprises said intermediate member and wherein said second end of said elongate body is mounted against said intermediate member, wherein said one or more light guides are mounted in said intermediate member to cooperate with said optical window.

5. The optical probe of claim 1, wherein at least a portion of said optical window and/or a further optical member adjacent said optical window is adapted to modify light passing through said optical window.

6. The optical probe of claim 5, wherein said optical window and/or said further optical member comprises or incorporates at least one lens.

7. The optical probe of claim 5, wherein said optical window and/or said further optical member incorporates or is associated with mirror surfaces configured to modify light passing through said optical window.

8. The optical probe of claim 5, wherein said optical window and/or said further optical member incorporates or is associated with a filter adapted to pass specific wavelengths of light while blocking others.

9. The optical probe of claim 1, wherein said ultrasonic transducer comprises one or more ceramic transducer elements and a reaction mass mounted against said one or more ceramic transducer elements.

10. The optical probe of claim 9, wherein said ultrasonic transducer elements and reaction mass are secured to said first end of said elongate body by means of a fastener passing therethrough.

11. The optical probe of claim 1, wherein at least a distal portion said one or more light guides extends substantially parallel to said elongate body.

12. The optical probe of claim 11, wherein said one or more light guides comprise one or more optical fibres.

13. The optical probe of claim 1, wherein said elongate body comprises a cylindrical member having a diameter less than the diameter of said optical window such that said elongate body cooperates with a central region of said optical window to transmit ultrasonic vibrations thereto.

14. The optical probe of claim 13, wherein said one or more light guides cooperate with a peripheral region of said optical window outside of said central region of said optical window.

15. The optical probe of claim 1, wherein a distal end of said one or more light guides is adapted to modify light passing therethrough.

16. The optical probe of claim 15, wherein said distal end of said one or more light guides comprises an interference lens and/or a filter.

* * * * *